United States Patent
Karrer

[11] 4,088,776
[45] May 9, 1978

[54] METHYLENE DIOXY-SUBSTITUTED BENZENE DERIVATIVES

[75] Inventor: Friedrich Karrer, Basel, Switzerland

[73] Assignee: Ciba-Geigy Corporation, Ardsley, N.Y.

[21] Appl. No.: 729,054

[22] Filed: Oct. 4, 1976

Related U.S. Application Data

[62] Division of Ser. No. 460,403, Apr. 12, 1974, Pat. No. 3,987,108.

[30] Foreign Application Priority Data

Apr. 18, 1973 Switzerland .................. 5636/73
Mar. 18, 1974 Switzerland .................. 3706/74

[51] Int. Cl.² .............................................. A01N 9/28
[52] U.S. Cl. ............................ 424/282; 260/340.5 R
[58] Field of Search ............... 260/340.5 R, 340.5; 424/282

[56] References Cited
U.S. PATENT DOCUMENTS 3,988,477 10/1976 Karrer et al. ............... 260/340.5 X Primary Examiner—Ethel G. Love
Attorney, Agent, or Firm—Harry Falber

[57] ABSTRACT

Compounds of the formula

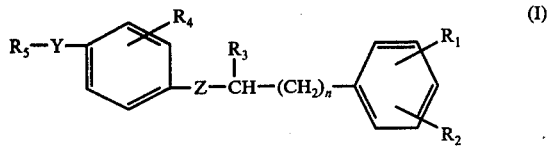

wherein
n represents the number 0 or 1,
Y represents —$CH_2$—, —N=N—, —$CH_2O$—, —NH—,

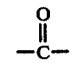

or the direct bond,
Z represents oxygen or sulphur,
$R_1$ represents hydrogen, $C_1$–$C_5$-alkyl; ethynyl, $C_1$–$C_5$-alkoxy, $C_3$–$C_5$-alkenyloxy, $C_3$–$C_5$-haloalkenyloxy, $C_3$–$C_5$-alkynyloxy, halogen, nitro, $C_2$–$C_5$-alkoxycarbonyl, $C_3$–$C_5$-alkenyloxycarbonyl, $C_3$–$C_5$-alkynyloxycarbonyl, $C_1$–$C_2$-alkanoyl, di(-$C_1$–$C_4$-alkyl)carbamoyl, $C_1$–$C_4$-alkylthio,
$R_2$ represents hydrogen, $C_1$–$C_5$-alkyl, $C_1$–$C_5$-alkoxy or halogen, or
$R_1$ and $R_2$ together represent a 3,4-methylenedioxy group,
$R_3$ represents hydrogen or $C_1$–$C_3$-alkyl,
$R_4$ represents hydrogen, $C_1$–$C_3$-alkyl or halogen,
$R_5$ represents cyclohexyl or the group

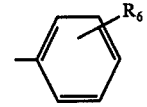

and
$R_6$ represents hydrogen, methyl, ethyl, halogen, methoxy or ethoxy and their use for the control of insects and members of the order acarina are disclosed.

10 Claims, No Drawings

METHYLENE DIOXY-SUBSTITUTED BENZENE DERIVATIVES

This is a division of application Ser. No. 460,403 filed on Apr. 12, 1974 now U.S. Pat. No. 3,987,108.

The present invention relates to phenyl-aralkyl ethers, phenyl-aralkyl thioethers and phenyl-aralkyl amines, to processes for their preparation and to their use in pest control.

The phenyl-aralkyl ethers, phenyl-aralkyl thioethers and phenyl-aralkyl amines have the formula

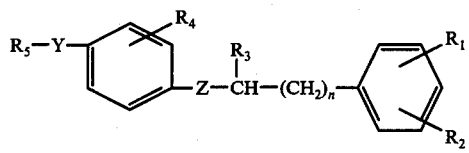 (I)

wherein
$n$ represents the number 0 or 1,
Y represents —$CH_2$—, —N=N—, —$CH_2O$—, —NH—,

or the direct bond,
Z represents oxygen or sulphur,
$R_1$ represents hydrogen, $C_1$–$C_5$-alkyl, ethynyl, $C_1$–$C_5$-alkoxy, $C_3$–$C_5$-alkenyloxy, $C_3$–$C_5$-haloalkenyloxy, $C_3$–$C_5$-alkynyloxy, halogen, nitro, $C_2$–$C_5$-alkoxycarbonyl, $C_3$–$C_5$-alkenyloxycarbonyl, $C_3$–$C_5$-alkynyloxycarbonyl, $C_1$–$C_2$-alkanoyl, di(-$C_1$–$C_4$-alkyl)carbamoyl, $C_1$–$C_4$-alkylthio,
$R_2$ represents hydrogen, $C_1$–$C_5$-alkyl, $C_1$–$C_5$-alkoxy or halogen, or
$R_1$ and $R_2$ together represent a 3,4-methylenedioxy group,
$R_3$ represents hydrogen or $C_1$–$C_3$-alkyl,
$R_4$ represents hydrogen, $C_1$–$C_3$-alkyl or halogen,
$R_5$ represents cyclohexyl or the group

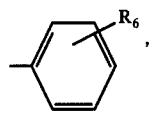

and
$R_6$ represents hydrogen, methyl, ethyl, halogen, methoxy or ethoxy.

By halogen is meant fluorine, chlorine, bromine or iodine. The alkyl, alkylthio, alkoxy, alkenyloxy, haloalkenyloxy or alkynyloxy groups given under $R_1$ are straight-chain or branched-chain. Examples of such groups are: methyl, ethyl, n-propyl, isopropyl, methylthio, methoxy, ethoxy, β-chloroallyloxy, γ-chloroallyloxy, allyloxy or propargyloxy. The alkyl, alkoxy, alkenyloxy, alkynyloxy parts of an alkoxycarbonyl, alkenyloxycarbonyl or alkynyloxycarbonyl or dialkylcarbamoyl group in the case of $R_1$ can be branched-chain or straight-chain. Examples of alkoxy, alkenyloxy, alkynyloxycarbonyl or dialkylcarbamoyl groups are: methoxycarbonyl, ethoxycarbonyl, propoxycarbonyl, isopropoxycarbonyl, alkoxycarbonyl, propargyloxycarbonyl or diethylcarbamoyl.

Preferred compounds of formula I are those wherein
$n$ represents the number 0,
Z represents oxygen or sulphur,
Y represents —$CH_2$—, —NH—,

or the direct bond,
$R_1$ represents hydrogen, fluorine, chlorine, bromine, iodine, methyl, ethyl, isopropyl, methoxy, ethoxy, methylthio, allyloxy, propargyloxy, carbomethoxy, carbethoxy, diethylcarbamoyl, nitro or acetyl,
$R_2$ represents hydrogen or methyl, or
$R_1$ and $R_2$ together represent the methylenedioxy group,
$R_3$ represents hydrogen, methyl or ethyl,
$R_4$ represents hydrogen or chlorine, and
$R_5$ represents cyclohexyl or unsubstituted phenyl.

The compounds of formula I are prepared, using methods known per se, by alkylation of a phenol or phenolate or of a thiophenol or thiophenolate II or IV with a halide III, in the presence of a base or of a proton acceptor:

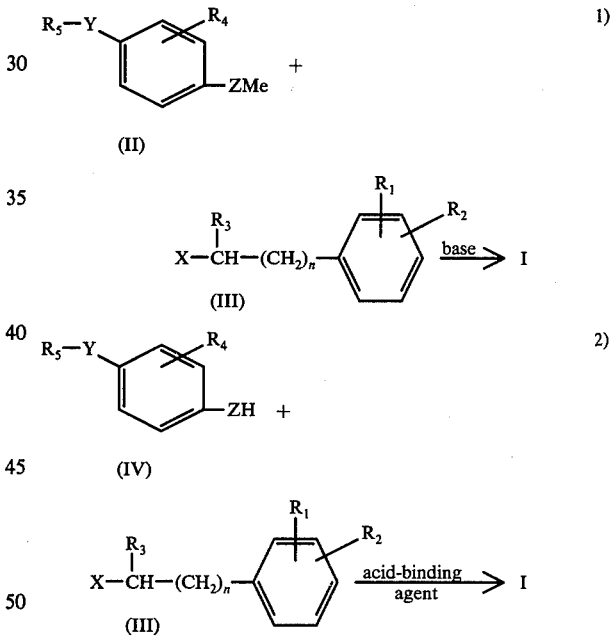

In formulae II to IV, the symbols $R_1$ to $R_5$, Z, Y and $n$ have the meanings given for formula I, and X stands for halogen, particularly for chlorine or bromine, and Me for a metal of the 1st or 2nd group of the periodic system, especially for sodium, potassium or calcium.

The starting materials of formulae II to IV are known and can be prepared by known methods.

Suitable acid-binding agents or bases are, e.g. tertiary amines such as trialkylamines, pyridine, dialkylanilines; also inorganic bases such as hydrides or hydroxides; alkoxides and carbonates of alkali metals and alkaline-earth metals.

Processes 1 and 2 are performed at a reaction temperature of between −10° and 130° C, preferably at between 10° and 80° C, under normal pressure, and in the presence of solvents or diluents. Suitable solvents or diluents are, e.g. ethers such as diethyl ether, diisopropyl ether, 1,2-dimethoxyethane, dioxane or tetrahydrofuran; N,N-dialkylated carboxylic acid amides such as dimethylformamide; aliphatic and aromatic hydrocarbons, particularly benzene, toluene, xylenes or ethyl benzene, or dimethylsulphoxide; ketones such as acetone, methyl ethyl ketone or cyclohexanone as well as hexamethylphosphoric acid triamide.

Furthermore, compounds of formuala I wherein Z denotes oxygen can be prepared according to the following reaction sequence:

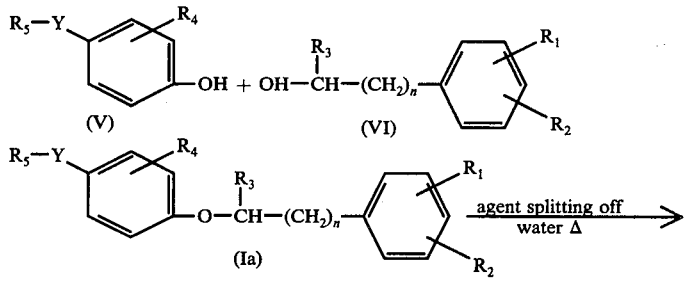

In formulae V, VI and Ia, the symbols $R_1$ to $R_5$ and $n$ have the meanings given for formula I. The starting materials of formulae V and VI are known and can be prepared by known methods.

In the above process, the condensation of a compound of formula V with a compound of formula VI is performed with the splitting-off of water preferably at a temperature of 60°–110° C. The employed agent splitting off water is preferably dicyclohexylcarbodiimide.

The compounds of formula I are suitable for the control of insects of the families:

Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae and Pulicidae, as well as acarids of the families:

Ixodidae, Argasidae, Tetranychidae and Dermanyssidae.

The insecticidal action of the said compounds can be appreciably widened and adapted to suit given circumstances by the addition of other insecticides and/or acaricides. Suitable additives are, for example:
organic phosphorus compounds,
nitrophenols and derivatives,
formamidines, ureas,
carbamates or
chlorinated hydrocarbons.

The compounds of formula I can be used on their own or together with suitable carriers and/or additives. Suitable carriers and additives may be solid or liquid, and they correspond to the substances common in formulation practice, such as, e.g. natural or regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice.

The agents according to the invention are prepared in a manner known per se by the intimate mixing and/or grinding of active substances of formula I with suitable carriers, optionally with the addition of dispersing agents or solvents which are inert to the active substances. The active substances can be obtained and used in the following forms:

solid preparation:- dusts, scattering agents, granulates, coated granulates, impregnated granulates and homogeneous granulates;

liquid preparations:

(a) water-dispersible active-substance concentrates: wettable powders, pastes or emulsions;

(b) solutions.

The content of active substance in the described agents is between 0.1 and 95%.

The active substances of formula I can be formulated, for example, as follows:

Dusts

The following substances are used in the preparation of a) a 5% dust, and b) a 2% dust:

(a)

5 parts of active substance,
95 parts of talcum;

(b)

2 parts of active substance,
1 part of highly dispersed silicic acid,
97 parts of talcum.

The active substances are mixed and ground with the carriers.

Granulate

The following substances are used to prepare a 5% granulate:

5 parts of active substance,
0.25 part of epichlorohydrin,
0.25 part of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The solution thus obtained is sprayed onto kaolin, and the acetone subsequently evaporated off in vacuo.

Wettable powder

The following constituents are used for the preparation of a) a 40%, b) and c) a 25%, and d) a 10% wettable powder:

(a)

40 parts of active substance,
5 parts of sodium lignin sulphonate,
1 part of sodium dibutyl-naphthalene sulphonate,
54 parts of silicic acid;

(b)

25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin;

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to prepare a) a 10% and b) a 25% emulsifiable concentrate (a)

10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

(b)

25 parts of active substance,
2.5 parts of epoxidised vegetable oil,
10 parts of an alkylarylsulphonate/fatty alcohol polyglycol ether mixture,
5 parts of dimethylformamide,
57.5 parts of xylene.

From these concentrates it is possible to prepare, by dilution with water, emulsions of any desired concentration.

Spray

The following constituents are used to prepare a 5% spray:

5 parts of active substance,
1 part of epichlorhydrin,
94 parts of ligroin (boiling limits 160° – 190° C).

EXAMPLE 1

Preparation of 1-benzyl-4-(4'-methyl)-benzyloxy-benzene 17.6 g of finely powdered anhydrous potassium carbonate is added to the solution of 18.8 g of 4-benzylphenol in 100 ml of anhydrous acetone, and the mixture heated to the reflux temperature of the acetone. After half an hour, an addition is made dropwise in the course of one hour of 14.1 g of α-chloro-p-xylene dissolved in 10 ml of acetone, and refluxing continued for a further 8 hours. In further processing, the reaction solution is filtered off from the solid phase, and the solvent removed in vacuo from the filtrate. The residue is dissolved in ether/hexane 1:3; this solution is washed four times with 10% sodium hydroxide solution, and subsequently with water and sodium chloride solution until neutral. After drying of the organic phase by means of sodium sulphate, the solvent is completely distilled off in vacuo, and the residue recrystallised in n-hexane to thus obtain colourless 1-benzyl-4-(4'-methyl)-benzyloxybenzene, M.P. 63° – 64° C.

Also the following compounds are prepared in the manner described above:

| Compounds | Physical data |
|---|---|
| 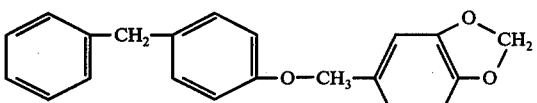 | M.P. : 83–85° C |
| 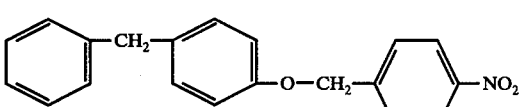 | M.P. : 65–66° C |
| 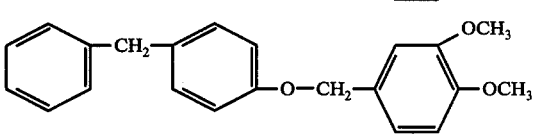 | M.P. : 60–62° C |

-continued
| Compounds | Physical data |
|---|---|
| 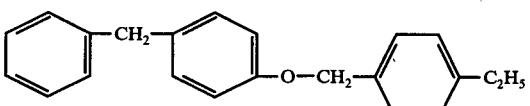 | $n_D^{20}$ : 1,5911 |
| 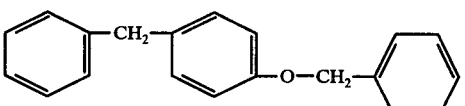 | M.P. : 51–52° C |
| 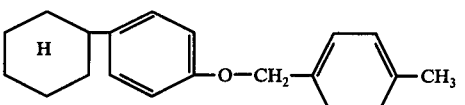 | M.P. : 86–87° C |
| 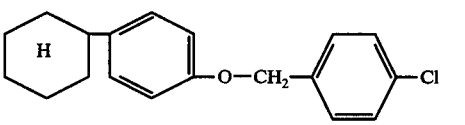 | M.P. : 101–103° C |
| 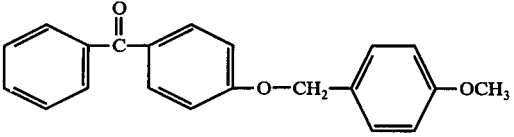 | M.P. : 112–113° C |
| 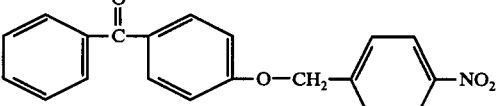 | M.P. : 135–137° C |
| 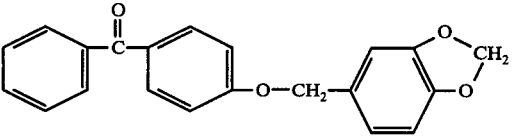 | M.P. : 103–104° C |
| 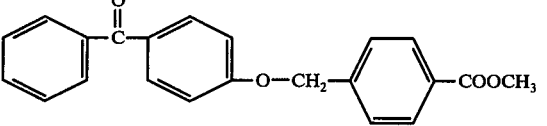 | M.P. : 128–130° C |
| 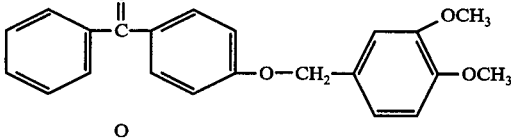 | M.P. : 106–108° C |
| 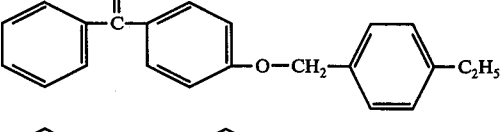 | M.P. : 93–94° C |
| 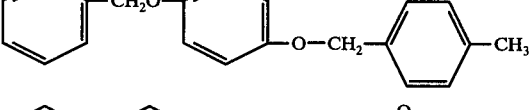 | M.P. : 114–115° C |
| 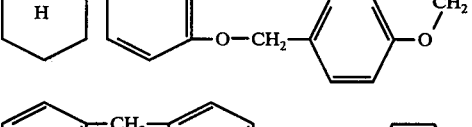 | M.P. : 73–75° C |
| 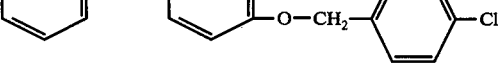 | M.P. : 63–64° C |

-continued

| Compounds | Physical data |
|---|---|
| Ph-CH₂-C₆H₄-O-CH₂-C₆H₄-F | M.P. : 45–46° C |
| Ph-CH₂-C₆H₄-O-CH₂-C₆H₄-Br | M.P. : 76–77° C |
| Ph-N=N-C₆H₄-O-CH₂-C₆H₄-CH₃ | M.P. : 114–115° C |
| Ph-CH₂-C₆H₄-O-CH₂-C₆H₄-J | M.P. : 85–86° C |
| Ph-NH-C₆H₄-O-CH₂-C₆H₄-CH₃ | M.P. : 77–78° C |
| Ph-CH₂-C₆H₄-O-CH₂-C₆H₄-C₃H₇(i) | $n_D^{20}$ : 1,5760 |
| Ph-CO-C₆H₄-O-CH₂-C₆H₄-Cl | M.P. : 89–90° C |
| Ph-CO-C₆H₄-O-CH₂-C₆H₄-CH₃ | M.P. : 106–108° C |
| Ph-C₆H₄-O-CH₂-C₆H₄-CH₃ | M.P. : 136–137° C |
| Ph-C₆H₄-O-CH₂-C₆H₄-Cl | M.P. : 144–145° C |
| Ph-CH₂O-C₆H₄-O-CH₂-C₆H₄-Cl | M.P. : 130–131° C |
| Ph-CH₂-C₆H₄-O-CH₂-C₆H₃(OCH₃) | M.P. : 65–66° C |
| Ph-CH₂-C₆H₄-O-CH₂-C₆H₃(CH₃)(CH₃) | $n_D^{20}$ : 1,5883 |

-continued
| Compounds | Physical data |
|---|---|
| 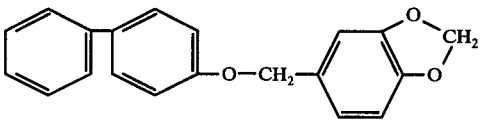 | M.P. : 143–145° C |
| 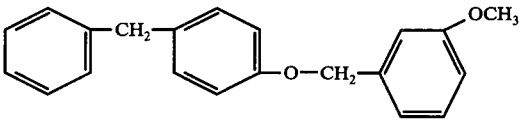 | $n_D^{20}$ : 1,6000 |
| 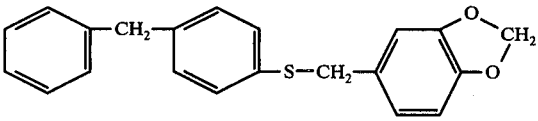 | M.P. : 63–64° C |
| 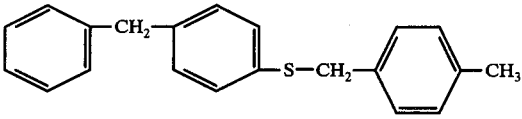 | M.P. : 54–55° C |
| 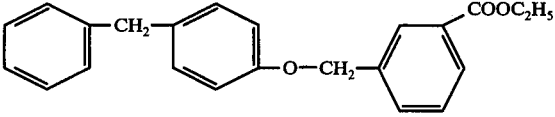 | $n_D^{20}$ : 1.5866 |
| 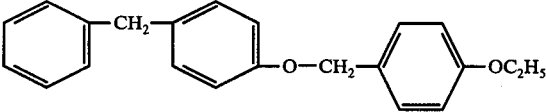 | M.P. : 72–73° C |
| 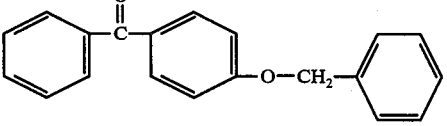 | M.P. : 79–81° C |
| 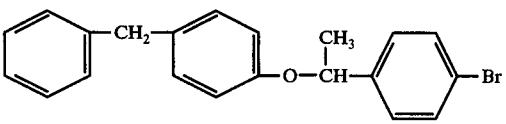 | M.P. : 49–50° C |
| 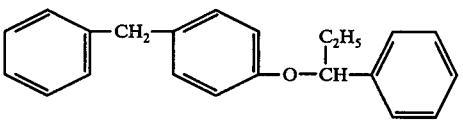 | |
| 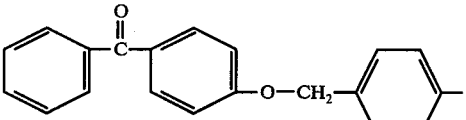 | M.P. : 102–103° C |
| 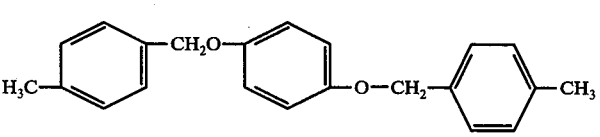 | M.P. : 144–145° C |
| 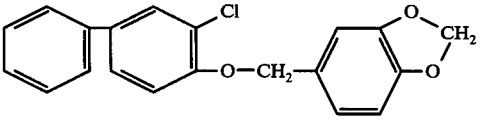 | M.P. : 117–118° C |
| 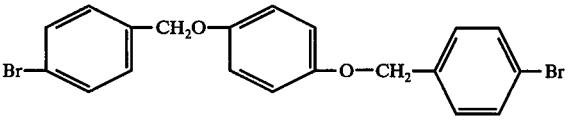 | M.P. : 187–188° C |

-continued

| Compounds | Physical data |
|---|---|
| 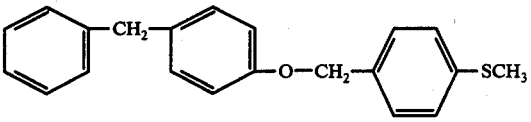 | M.P.: 91–92° C |
| 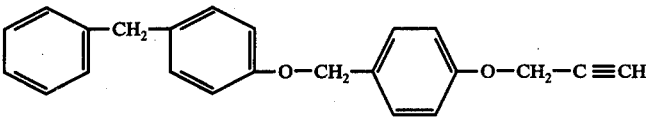 | M.P.: 75–76° C |
| 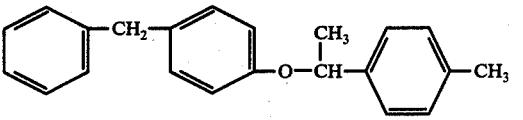 | $n_D^{20}$: 1,5832 |
| 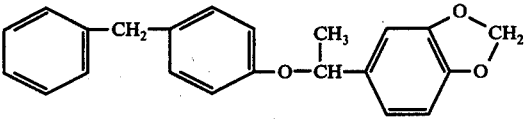 | |
| 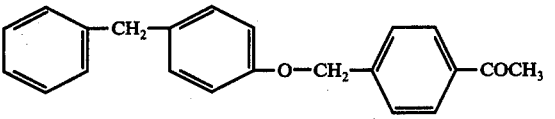 | M.P.: 97–98° C |
| 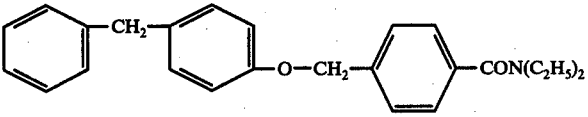 | M.P.: 66–68° C |

EXAMPLE 2

(A) Contact action on Dysdercus-fasciatus larvae

A specific amount of a 0.1% acetonic active-substance solution (corresponding to 10 mg of active substance per square meter) was transferred by pipet to an aluminium dish and uniformly distributed. After evaporation of the acetone, 10 larvae in the 5th stage of Dysdercus fasciatus were placed into the treated dish containing feed and moist cotton wool. The dish was then covered with a perforated lid. After about 10 days, i.e. as soon as the control insects had moulted into adults, the test insects were examined to determine the number of normal adults.

Compounds according to Example 1 exhibited a good action in the above test.

(B) Contact action on Aedes-aegypti larvae

About 20 two-day-old larvae of the yellow-fever mosquito (Aedes aegypti) were placed in position in a beaker containing a solution of the active substance (concentration 5 ppm). The beaker was then covered with a perforated lid. After the control insects had moulted into adults, the test insects were examined and the percentage of normal adults in comparison with the control adults determined.

Compounds according to Example 1 exhibited a good action in the above test.

(C) Contact action on Tenebrio-molitor pupae

A specific amount of a 0.1% acetonic active-substance solution corresponding to 10 mg of active substance per square meter was transferred by pipet into an aluminium dish and uniformly distributed. After evaporation of the acetone, 10 freshly formed pupae were placed on the treated surface, and the dish covered with a perforated lid. After the control insects had left the cocoon as imagines, the test insects were examined to determine the number of normal adults.

Compounds according to Example 1 exhibited a good action in the above test.

EXAMPLE 3

(A) Action against Musca domestica

An amount in each case of 50 g of CSMA maggot substrate was weighed off in beakers. For each active substance, 2.5 ml of a 1% acetonic solution of the respective substance was transferred twice to 50 g of maggot substrate each time. After a thorough mixing of the treated substrate, the solvent was allowed to evaporate off. There were then deposited per active substance in each case 25 one-, two- and three-day-old maggots and about 50 fly eggs. After completion of pupation, the pupae were flushed out and counted. After a period of ten days, the number of emerged flies was determined and hence any effect on metamorphosis established.

Compounds according to Example 1 exhibited in this test a good action against Musca domestica.

(B) Action against Ephestia kuhniella 50 g of wheat flour was made up in two beakers with a specific amount of active substance to give a 5% dust, the concentration thus being 0.05%. Into each beaker (25 g of flour) were placed 10 larvae of Ephestia kuhniella. The course of population was ascertained over a period of 8 weeks and the number of moths determined.

Compounds according to Example 1 exhibited a good action in the test against Ephestia kuhniella.

EXAMPLE 4

Action against red spider mites

*Phaseolus vulgaris* (bush beans) were infested, 12 hours before the test for acaricidal action, with an infested piece of leaf from a mass culture of Tetranychus urticae. The transferred mobile stages were sprayed with the emulsified test preparations, at a concentration of 0.04%, by means of a chromatography-sprayer in a manner ensuring no running off of the spray liquor. An assessment was made after 2 to 7 days, by examination under a binocular, of the living and of the dead larvae, adults and eggs, and the results expressed in percentages. The treated plants were kept during the holding time in greenhouse compartments at 25° C.

The compounds according to Example 1 exhibited in the above test a good action against eggs, larvae and adults of Tetranychus urticae.

What we claim is:

1. A compound of the formula

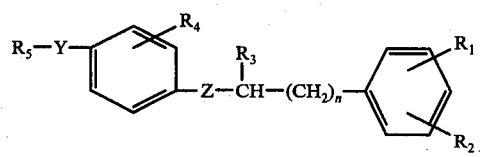

(I)

wherein $n$ represents the number 0 or 1,

Y represents —CH$_2$—, —CH$_2$O—,

or the direct bond,

Z represents oxygen or sulphur,

R$_1$ and R$_2$ together represent a 3,4-methylenedioxy group,

R$_3$ represents hydrogen or C$_1$–C$_3$-alkyl,

R$_4$ represents hydrogen, C$_1$–C$_3$-alkyl or halogen,

R$_5$ represents cyclohexyl or the group

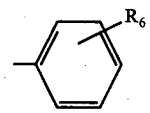

and

R$_6$ represents hydrogen, methyl, ethyl, halogen, methoxy or ethoxy.

2. The compound according to claim 1 wherein $n$ represents the number 0,

Z represents oxygen or sulphur,

Y represents —CH$_2$—,

or the direct bond,

R$_1$ and R$_2$ together represent the methylenedioxy group,

R$_3$ represents hydrogen, methyl or ethyl,

R$_4$ represents hydrogen or chlorine, and

R$_5$ represents cyclohexyl or unsubstituted phenyl.

3. 1-Benzyl-4-(3',4'-methylenedioxy)-benzyloxybenzene according to claim 2.

4. 4-(3',4'-Methylenedioxy)-benzyloxybenzophenone according to claim 2.

5. 1-Cyclohexyl-4-(3',4'-methylenedioxy)-benzyloxybenzene according to claim 2.

6. 4-(3',4'-Methylenedioxy)-benzyloxydiphenyl according to claim 2.

7. 1-Benzyl-4-(3',4'-methylenedioxy)-benzylthiobenzene according to claim 2.

8. 1-Benzyl-4-[1'-(3'',4''-methylenedioxy-phenyl)-ethoxy]-benzene according to claim 2.

9. An insecticidal or acaricidal agent containing an insecticidal or acaricidal effective amount of a compound of claim 1 together with a suitable carrier therefor.

10. A method for the control of insects or members of the order Acarina which comprises applying to the locus thereof an insecticidal or acaricidal effective amount of a compound of claim 1.

* * * * *